United States Patent [19]

Smart

[11] 3,963,767
[45] June 15, 1976

[54] METHOXYPERFLUOROCYCLOALKENIUM HEXAFLUOROANTIMONATE SALTS

[75] Inventor: Bruce Edmund Smart, Wilmington, Del.

[73] Assignee: E. I. Du Pont de Nemours and Company, Wilmington, Del.

[22] Filed: Sept. 3, 1975

[21] Appl. No.: 609,997

[52] U.S. Cl. ............................ 260/446; 252/431 R; 260/429 CY
[51] Int. Cl.² ............................................ C07F 9/90
[58] Field of Search .................... 260/446, 429 CY; 252/431 R

[56] References Cited
UNITED STATES PATENTS
3,379,746  4/1968  Weil .............................. 260/446 X OTHER PUBLICATIONS
Chemical Abstracts, V72,89557u (1970).
Chemical Abstracts, V78,97154z (1973).
J.A.C.S. V91,415–419 (1969).

*Primary Examiner*—Helen M. S. Sneed
*Attorney, Agent, or Firm*—Anthony P. Mentis

[57] ABSTRACT

Alkoxyfluorocycloalkenium hexafluoroantimonate salts are stable at room temperature. They catalyze the polymerization of tetrahydrofuran. Exemplary is 1-methoxy-2,3,4,4-tetrafluorocyclobutenium hexafluoroantimonate of the formula

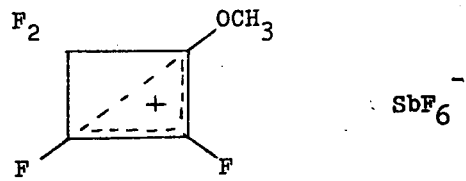

15 Claims, No Drawings

METHOXYPERFLUOROCYCLOALKENIUM HEXAFLUOROANTIMONATE SALTS

BACKGROUND OF THE INVENTION

1. Field of the Invention

This invention relates to alkoxyfluorocycloalkenium hexafluoroantimonate salts of the formula

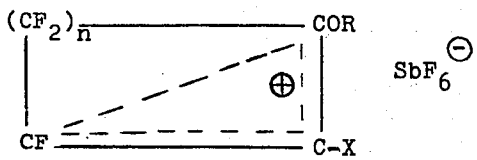

wherein R is lower alkyl, X is F, Cl, Br, or OR and n is 0, 1, or 2. These salts are stable at room temperature and catalyze tetrahydrofuran polymerization.

2. Prior Art

Sargeant et al, J.A.C.S. 91, 415 (1969) report the hexafluoroantimonate salt of perflurocyclopropene is not stable in air at room temperature. Law et al, J. Org. Chem. 38, 768 (1973) have prepared hexafluoroantimonate salts of fluorochlorocyclopropene but do not show any fluorinated alkoxy compounds. Scherer et al, Chem. Ber. 99, 1966 (1966)describe alkoxypolyfluorocyclobutene and cyclopentene but no hexafluoroantimonate salts.

DESCRIPTION OF THE INVENTION

There have now been obtained alkoxyfluorocycloalkenium hexafluoroantimonate salts of the formula

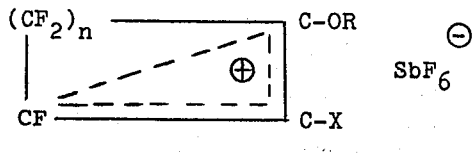

wherein R is a 1–4 carbon alkyl, X is F, Cl, Br, or OR, n is 0, 1, or 2 and the dotted lines indicate ring unsaturation.

The salts are prepared by reaction of $SbF_5$ with fluorinated cyclic vinyl ethers, i.e. 1-alkoxyfluorocyclopropene, butenes, or pentenes of the formula

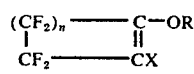

wherein R, X and n are as defined above.

No special requirements as to reaction conditions are needed except that extraneous reactants, e.g., hydroxylcontaining compounds such as water should be absent and the temperature should be kept below about 70°.

An inert solvent and low temperatures (e.g. −78°) should be used when a fluorinated cyclopropene (n=0) is used since its reaction with $SbF_5$ in the absence of a solvent is explosive.

Solvents which can be used in this reaction, such as sulfur dioxide, sulfuryl chlorofluoride, or sulfuryl fluoride, are recommended since the products precipitate during the course of the reaction and efficient mixing becomes difficult in the absence of added solvent. When sulfur dioxide solvent is employed, the vinyl ether is added to a solution of $SbF_5$ at −78°to −10°; the solvent is then evaporated and the pure cation salt is deposited.

The fluorinated cyclic vinyl ethers where n is 1 or 2 are known compounds. The cyclopropenyl vinyl ethers, i.e., n = 0, are obtained by adding an alkali metal alkoxide (MOR where R is methyl, ethyl, propyl or butyl and M is Na, Li, K) to a known cyclopropene of the formula

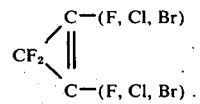

For example

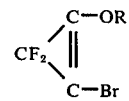

is available from 1,2-dibromo-3,3-difluoropropene by reaction with an alkali metal alkoxide.

The 3-membered ring cation salts are stable in the solid state at 80°and are therefore more stable than the previously reported cyclopropenium hexafluoroantimonates of Law et al. They are also stable in $SO_2$ solution at 60°. The 4- and 5-membered ring salts slowly decompose at 60°in solution and are stable in the solid state below 60°. The cation salts of each ring system are hydrolytically unstable.

The free cation structures were confirmed by nmr analyses and quenching experiments. Characteristic large observed deshieldings of fluorine chemical shifts in the salts exclude the possibility of simple ether-$SbF_5$ complexes. The 4- and 5-membered ring species form cycloalkenones by aqueous hydrolysis and form phenylcycloalkenones by electrophilic substitution on benzene.

Specific Embodiments of the Invention

In the following illustrative examples all parts are by weight and all temperatures are Centigrade unless otherwise stated.

EXAMPLE 1

1-Methoxy-2,3,4,4-tetrafluorocyclobutenium Hexafluoroantimonate (2)

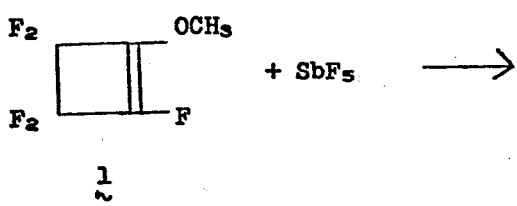

To 0.10 mole of SbF$_5$ in 50 ml of SO$_2$ at −78° under N$_2$, 0.10 mole (17.4 g) of 1-methoxy-2,3,3,4,4-pentafluorocyclobutene (1) was added dropwise. After complete addition, the SO$_2$ solvent was allowed to evaporate in a stream of N$_2$ while the reaction mixture was warmed to room temperature. A quantitative yield of crystalline 2 was obtained. This solid is stable at room temperature under nitrogen gas. Variable temperature nmr studies of 2 in SO$_2$ revealed the presence of two isomers (71%, 29%) which differ only by the methoxy group conformation. Nmr 2 (SO$_2$, ext ref): $^1$H$\delta$(45°) 5.03 (br s), (−35°) major isomer: $\delta$ 5.04 (br t), $^{19}$F (−35°) $\phi$ −34.9 (d of t, 1, J = 15.2, 9.2 Hz), −99.7 (d of t, 1, J = 15.2, 12.1 Hz), −105.8 (d of d, 2, J =12.1, 9.2 Hz); minor isomer; $^1$H $\delta$ (−35°) 4.97 (br s), $\phi$−36.6 (d of t, 1, J ~ 14, 7 Hz), ~−100 (overlapping m, 3).

Compound 2 was also obtained by reaction under N$_2$ of 35 g (0.162 mole) of SbF$_5$ with 26.1 g (0.15 mole ) of 1 during which reaction temperature rose to 70-75°.

SbF$_5$ while the reaction temperature was kept below 20°. After the addition was completed, 42.4 g of white crystalline 2 was obtained. This solid was cautiously added to iced water; the insoluble organic product was separated, dried, and distilled to give 10.8 g of 3: bp 54°(7 mm); ir (neat) 1,825 cm$^{-1}$ (C = 0), 1,680 cm$^{-1}$ (C = C); nmr (CCl$_4$) $^1$H $\delta$ 4.48 (d, J ~1.5 Hz), $^{19}$F $\phi$ − 115.4 (d, 2, J = 21.5 Hz), −124.3 (t of q, 1, J = 2.5, 1.5 Hz).

Anal. Calcd. for C$_4$H$_3$F$_2$O$_2$: C, 39.49; H, 1.98; F, 37.48

Found: C, 39.59; H, 2.10; F, 38.34

When the antimonate salt obtained according to the immediately preceding process was exposed to moist air it also hydrolyzed but less completely to the cyclobutenone.

EXAMPLE 2

1-Methoxy-2-chloro-3,4,4-trifluorocyclobutenium Hexafluoroantimonate

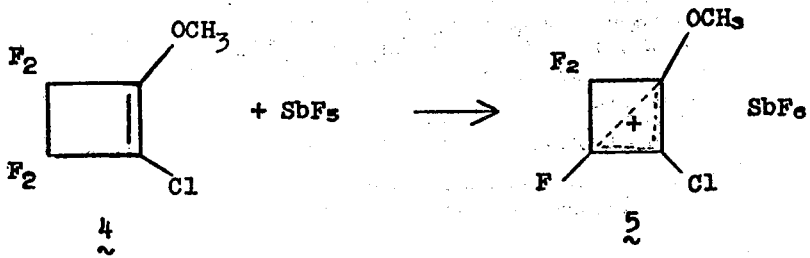

A sample of the solidified reaction mixture was pressed on a filter paper to purify it.

Anal. Calcd. for C$_5$H$_3$F$_{10}$OSb: C, 15.37; H, 0.77; F, 48.61

Found: C, 14.92; H, 1.03; F, 49.23

The nmr samples of 2 in SO$_2$ were heated from −40°to 60°. At 60° for several minutes, 2 slowly decomposed.

The antimonate (2) solution in SO$_2$ prepared substantially as above was chilled to −78° and added cautiously to 200 ml of vigorously stirred iced water. After warming to room temperature and stirring until all the solid dissolved, 25 ml of methylene chloride was added. The organic phase was withdrawn, washed with saturated aqueous sodium chloride, dried (MgSO$_4$), and distilled to give 3.9 g of 3-methoxy-2,4,4-trifluorocyclobut-2-en-1-one (3): bp 58°(10 mm).

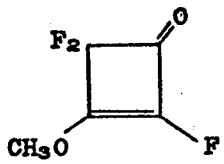

The latter compound was also obtained by preparation of the antimonate without solvent as follows:

Ether 1 (15.4 g, 0.10 mole obtained as described by J. T. Burr, et al., J. Amer. Chem. Soc., 72, 4480 [1950]) was added dropwise to 25 g (0.115 mole) of A quantitative yield of 5 was obtained from 0.10 mole of 4, 1-methoxy-2-chloro-3,3,4,4-tetrafluorocyclobutene (prepared as described by J. D. Park, et al., J. Amer. Chem. Soc., 73, 2343 [1951]), and 0.10 mole of SbF$_5$ following the procedure of the first part of Example 1. Solid 5 is stable at room temperature under N$_2$ and is a mixture of two isomers (52%, 48%)in SO$_2$ (variable temperature nmr). Nmr (SO$_2$, ext ref) $^1$H $\delta$ (50°) 5.11 (s), $\delta$ (−30°) major isomer 5.22 (br s), $^{19}$F $\phi$ −24.8 (t, J = 8.8 Hz), −104.6 (d, J = 8.8 Hz); minor isomer $\delta$(−30°) 5.07 (br s), $^{19}$F $\phi$−26.4 (t, J = 8.4 Hz), −98.1 ( d, J = 8.4 Hz).

This antimonate was also obtained as follows: To 25 g (0.115 mole) of SbF$_5$ chilled in an ice bath was added 19.0 g (0.1 mole) of 4. After the addition of 4 was completed, 44 g of solid 5 was recovered. This solid was hydrolyzed, worked up as before, and distilled to give 2.1 g of 4: bp 40°(30 mm) and 6.4 g of 2-chloro-4,4-difluoro-3-methoxycyclobut-2-en-1-one (6) of the formula

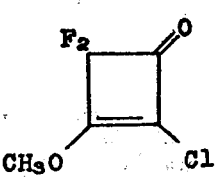

bp 68° (6.5 mm); ir (neat) 1,804 cm⁻¹ (C=O), 1,6525 cm⁻¹ (C=C); nmr (CCl₄) ¹H δ 4.48 (s), ¹⁹F φ −113.2 (s).

Anal. Calc'd for $C_5H_3ClF_2O_2$: C, 35.64; H, 1.79; F, 22.55

Found: C, 35.76; H, 1.90; F, 22.67.

The product 6 was also obtained by hydrolysis of the antimonate salt obtained by use of SO₂ as a solvent.

EXAMPLE 3

1,2-Dimethoxy-3,4,4-trifluorocyclobutenium Hexafluoroantimonate

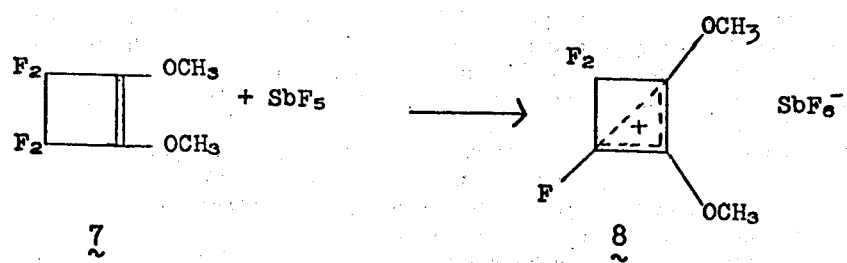

Following the procedure of the first part of Example 1 using 0.1 mole each of SbF₅ and 3,3,4,4-tetrafluoro-1,2-dimethoxycyclobutene 7 (obtained as described by Park et al., J. Amer. Chem. Soc. 71, 2337 (1949), the antimonate salt obtained was characterized as follows:

Variable temperature nmr indicated two isomers (68%, 32%) were present: nmr (SO₂, ext. ref) ¹H δ (50°) 4.76 (d, 1, J ~ 0.8 Hz), 4.03 (d of t, I, J = 1.5, 0.8 Hz); δ (−50°) major isomer 4.79 (d, 1, J = 0.8 Hz), 4.02 (m) ¹⁹F φ −51.2 (t of m, 1, J = 10.9 Hz), −102.4 (d of m, 2, J 10.9 Hz); minor isomer ¹H (−50°) δ 4.70 (br s, 1), 4.05 (m, 1), ¹⁹F φ −49.8 (t of m, 1, J = 10.7 Hz), −95.5 (d of m, 2, J = 10.7 Hz).

The antimonate salt was also obtained by direct reaction without solvent. To 30.5 g of the salt, ice water was used to give methoxy cyclobutenones of the structures

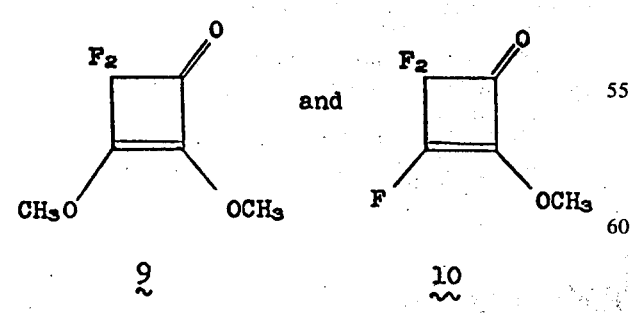

a total of 10.4 g of product was distilled to give 1.7 g of 95% 10 and 5% 7: bp 73°-75° (100 mm); 2.5 g of 67% 10, 33% 7: bp 72° (70 mm); 1.1 g of 80% 7, 20% 10: bp 65°-48° (40-5 mm); 0.2 g of 80% 9: bp 58°-68° (3 mm); and 1.8 g of 85% 9: bp 69° (3 mm); ir (neat) 1,798 cm⁻¹ (C=O), 1,643 cm⁻¹ (C=C); nmr (CCl₄) δ =H 4.15 (s, 1), 4.22 (s, 1), ¹⁹F φ −111.4 (s). Pure 10 was collected by preparative vapor phase chromatography: ir (neat) 1,810 cm⁻¹ (C=O), 1,690 cm⁻¹ (C=C); nmr (CCl₄) ¹H 4.23 (d of t, J = 0.8, 0.6 Hz), ¹⁹F φ−112.1 (m).

Anal. Calc'd for 10 $C_5H_3F_3O_2$: C, 39.49; H, 1.98

Found: C, 39.40; H, 2.01

Antimonate salt from SO₂ was hydrolyzed and worked up in the same manner to give the two products from which pure 9 bp 52° (0.8 mm) was obtained.

Anal Calc'd for 9 $C_6H_6F_2O_3$: C, 43.91; H, 3.69; F, 23.15

Found: C, 44.01; H, 3.72; F, 22.36

EXAMPLE 4

1-Methoxy-2,3,4,4,5,5-hexafluorocyclopentenium Hexafluoroantimonate

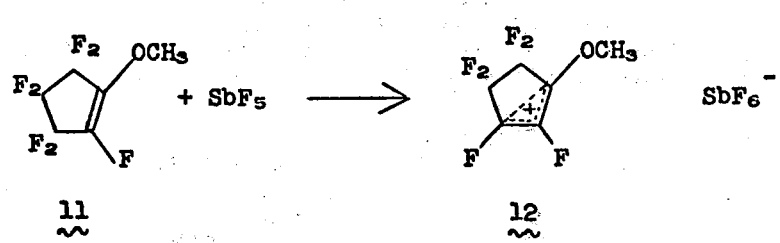

A solution of 24 g (0.11 mole) of SbF₅ in 50 ml of SO₂ was treated dropwise with 22.4 g (0.10 mole) of 11 (1-methoxyperfluorocyclopentene, Stockel, et al., Can J. Chem., 42, 2880 [1964]) and the SO₂ removed to give the salt 12.

This salt was hydrolyzed by reaction with water to give 3-methoxyperfluorocyclopent-2-en-1-one, 13 which was prepared by Stockel, ibid, by another method.

EXAMPLE 5

Methoxytrifluorocyclopropenium Hexafluoroantimonate

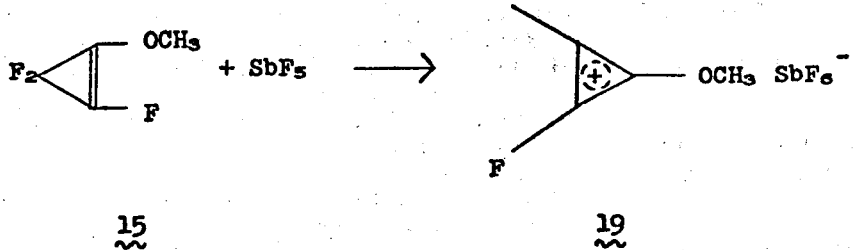

15 19

A solution of 12 g (0.055 mole) of SbF₅ in 25 ml of SO₂ at −78° was treated dropwise with 6.2 g (0.05 mole) of 1-methoxytrifluorocyclopropene, 15, while the reaction temperature was kept below −65°. After warming to room temperature and evaporation of the SO₂ solvent, 17.6 g of cream colored, extremely hydroscopic solid 19 was obtained: nmr (ext ref., −60° to 50°) $^1$H δ 4.49 (s), $^{19}$F φ −84.7 (s).

1-Methoxytrifluorocyclopropene (15) was obtained from tetrafluorocyclopropene, 14, (Sargeant et al., J. Amer. Chem Soc., 91, 415 [1969]) as follows:

A slurry of 15.1 g (0.28 mole) of sodium methoxide in 250 ml of dry diglyme at ca. −70° was slowly treated with 32.0 g (0.286 mole) of 14 while the reaction temperature was kept below ca. −60°. After warming to room temperature and stirring 1 hr., the reaction mixture was evacuated at 20 mm through a −78° trap. The trap material was distilled to afford 18.7 g of 15: bp 67°–69°. Analysis of this compound prepared in a similar way was ir (neat) 1907 cm$^{-1}$ (C=C); nmr (CCl₄) $^1$H δ 3.68 (S), $^{19}$F 100 −93.1 (d, 2, J = 48.2 Hz), −154.6 (t, 1, J = 48.2 Hz). A further sample had mass spec (P) calc'd 124.0136, found 124.011. Caution: 15, 1-methoxytrifluorocyclopropene, is exceedingly reactive; it must be prepared under anhydrous conditions, purified immediately, and stored as a solid at −78° under nitrogen. Sodium methoxide and SbF₅ react explosively with 15 in the absence of diluents; 15 is volatile and flashes into a black mushroom cloud in an open flame; and 15 is too unstable for combustion analysis. When mixed with water, it decomposes violently.

EXAMPLE 6

Methoxychlorofluorocyclopropenium Hexafluoroantimonate

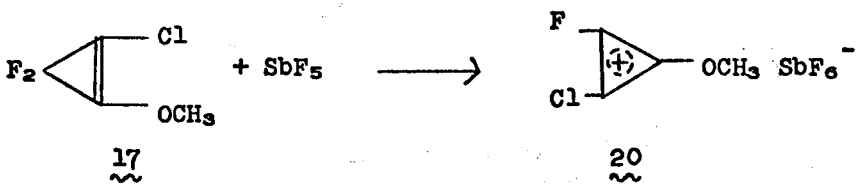

17 20

The reaction of 1-methoxy-2-chlorodifluorocyclopropene, 17, (0.05 mole) with 0.05 mole of SbF₅ as in Example 5 gave 16.4 g of very pale yellow, hygroscopic solid 20 which is stable at room temperature under N₂: nmr (SO₂, ext ref, −60° to 50°) $^1$H δ 4.63 (s), $^{19}$F φ −80.95 (s).

1-Methoxy-2-chlorodifluorocyclopropene was prepared from 1,2-dichloro-3,3-difluorocycloprepene (16) (Tobey et al., J. Amer. Chem. Soc., 88, 2241 [1966]) as follows:

A mixture of 16.2 g (0.3 mole) of sodium methoxide in 150 ml of dry diglyme was treated dropwise with 43.5 g (0.3 mole) of 16 while the reaction temperature was kept below −60°. After stirring 1 hr at room temperature, the reaction mixture was evacuated through a −78° trap at 10 mm. The crude product was redistilled to give 33.1 g of 17: bp 58–62 inches (mostly 61°–62°) (150 mm).

Anal. Calc'd for C₄H₃ClF₂O: C, 34.19; H, 2.15; F, 27.14
Found: C, 34.26; H, 2.43; F, 27.20

EXAMPLE 7

Dimethoxyfluorocyclopropenium Hexafluoroantimonate

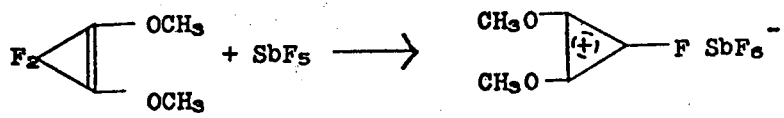

18 21

1,2-Dimethoxydifluorocyclopropene, 18, (0.02 mole) and 0.02 mole of SbF₅ in 10 ml of SO₂ were reacted as in Example 5 to give 6.3 g of stable, pale yellow, hygroscopic solid 21; nmr (SO₂, ext ref, 37°) $^1$H δ 4.30 (s), $^{19}$F −102.9 (s).

1,2-Dimethoxydifluorocyclopropene, 18, was prepared from tetrafluorocyclopropene, (14—see Example 5) as follows:

A slurry of 21.6 g (0.4 mole) of sodium methoxide in 200 ml of dry diglyme at ca. −70° was treated slowly with 22.4 g (0.2 mole) of 14. Upon slowly warming to room temperature, the reaction mixture noticeably exothermed and was immediately chilled in an ice bath. After stirring ca. 30 min. at 0° and an additional 30 min. at room temperature, the product was flash distilled at 20 mm into a −78° trap. The trap content was redistilled to give 13.1 of crude 18: bp 52°–55° (60 mm), ir (neat) 1,895 cm$^{-1}$ (C=C); nmr (CCl$_4$) $^1$H δ 3.84 (s), $^{19}$F φ −93.5 (s). Pure 18 was obtained after redistillation: bp 74°(80 mm), mass spec 136 (P). The compound is too unstable for combustion analysis. It is a stable colorless solid at −70° but at room temperature it rapidly reddens and decomposes. Water violently decomposes 18.

The compounds of this invention are reactive, e.g., the compounds of Example 1 and 2 react with benzene to give the corresponding 3-phenyl-perhalocyclobut-2-en-1-one, demonstrated as follows: A solution of 0.1 mole of 2 (or 5) in 50 ml of SO$_2$ at −40° to −45° was treated dropwise with 10 g (0.13 mole) of benzene. A yellow-orange color of precipitate formed. The SO$_2$ was slowly evaporated and the product was hydrolyzed by stirring with 150–250 ml of water. The resultant red-orange organic layer was taken up in 25–30 ml of methylene chloride and dried (MgSO$_4$). From 2 it was distilled to give 13.2 g of 3-phenyl-2,4,4-trifluorocyclubut-2-en-1-one: bp 56°(0.4 mm), mp 36.5°–37.5°; ir (mull) 1,806 cm$^{-1}$ (C=O), 1,650 cm$^{-1}$, 1,595 cm$^{-1}$ (C=C); nmr (CCl$_4$) $^1$H δ 7.60 (m), $^{19}$F φ − 101.2 ($t$, 1, J = 23.1 Hz), −113.0 ($d$, 2, J = 23.1 Hz).

Anal. Calc'd for C$_{10}$H$_5$F$_3$O: C, 60.62; H, 2.54; F, 28.76;
Found: C, 60.81; H, 2.61; F, 28.69.

From 5, the residual oil slowly crystallized to give 16.5 g (77%) of 2-chloro-3-phenyl-4,4-difluorocyclobut-2-ene-1-one: mp 77.5°–78°, ir (mull) 1,805 cm$^{-1}$ (C=O), 1,597 cm$^{-1}$ (C=C); nmr (CCl$_4$) $^1$H δ 7.5–8.1 (m), $^{19}$F φ −110.5 (s).

Anal. Calc'd for C$_{10}$H%ClF$_2$O: C, 55.97; H, 2.35; F, 17.71
Found: C, 56.23; H, 2.44; F, 17.64.

The salts are stable at room temperature and generally 60° or higher. The compound of Example 1 (2) is stable below 60° but at 60°–130°, perfluorocyclobutene and perfluorocyclobutenone were formed. The compound of Example 3 (8) melted at 80°–100° with some decomposition. The compounds of Examples 5 and 6 (19 and 20) were unchanged after heating at 60°. The compound of Example 6 (19) under Ar was placed in an oil bath at 80°. The sample rapidly melted but no decomposition was evident. After 10 min. at 80°, the sample was allowed to cool to room temperature and it resolidifed. The sample was unchanged by nmr.

The salts are also effective polymerization catalysts for tetrahydrofuran, as shown: Anhydrous tetrahydrofuran (10 g) was treated with ca. 0.3 g of 2 under N$_2$. The catalyst immediately dissolved and the solution became noticeably viscous after 5 minutes. After 15 minutes the clear colorless mixture was no longer free flowing. After 1 hour the clear mixture was very pale yellow, and after 16 hours a dark brown taffy-like material formed. This material was boiled in dilute aqueous ammonia (no melting); washed with water, and air dried to give 8.8 g of cream-colored solid polymer: inherent viscosity (0.1 wt % in hexafluoroisopropanol at 25°) = 1.25.

When the above procedure was repeated with 10 g of anhydrous tetrahydrofuran and ca. 0.3 g of 19, after 16 hours, a dark brown rubbery plug of polymer formed. After boiling with aqueous ammonia (no melting), washing with water, and air dried, 7.5 g of cream-colored solid polymer resulted; inherent viscosity (0.1 wt % vol in hexafluoroisopropanol at 25°) = 1.29.

In place of the methoxyfluorocycloalkenes as described in the examples, the corresponding ethoxy, n-and iso-propoxy, n-, iso- and tert-butoxy can be used. They are readily obtained by use of alkali metal alkoxides of higher alkyls, e.g., Na, K or Li ethoxide, propoxide or butoxide.

The salts of this invention are useful room temperature catalysts for tetrahydrofuran (THF) polymerization. They give better control of polymerization than antimony pentafluoride which is a liquid and must be employed at low temperature. The resultant THF polymer is particularly useful for "block" polymerizations, such as in the preparation of elastomeric materials.

I claim:
1. A compound of the formula

$$(CF_2)_n \begin{array}{c} \text{———COR} \\ \text{⊕} \\ \text{———C-X} \end{array} \quad SbF_6^-$$

(from CF to C-X)

wherein
R is alkyl of 1–4 carbons;
X is F, Cl, Br or OH;
$n$ is 0, 1 or 2; and
the dotted lines indicate ring unsaturation.
2. A compound of claim 1 where $n = 0$.
3. A compound of claim 1 where $n = 1$.
4. A compound of claim 1 where $n = 2$.
5. A compound of claim 1 where R = methyl.
6. A compound of claim 1 where X = fluorine.
7. A compound of claim 1 where X = chlorine.
8. A compound of claim 1 where X = methoxy.
9. The compound of claim 1 which is 1-methoxy-2,3,4,4-tetrafluorocyclobutenium hexafluoroantimonate.
10. The compound of claim 1 which is 1-methoxy-2-chloro-2,3,4,4-tetrafluorocyclobutenium hexafluoroantimonate.
11. The compound of claim 1 which is 1,2-dimethoxy-2,3,4,4-tetrafluorocyclobutenium hexafluoroantimonate.
12. The compound of claim 1 which is 1-methoxy-2,3,4,4,5,5-hexafluorocyclopentenium hexafluoroantimonate.
13. The compound of claim 1 which is methoxytrifluorocyclopropenium hexafluoroantimonate.
14. The compound of claim 1 which is methoxychlorofluorocyclopropenium hexafluoroantimonate.
15. The compound of claim 1 which is dimethoxyfluorocyclopropenium hexafluoroantimonate.

* * * * *